United States Patent [19]
Ono et al.

[11] Patent Number: 4,500,636
[45] Date of Patent: Feb. 19, 1985

[54] SILVER HALIDE PHOTOGRAPHIC LIGHT-SENSITIVE MATERIAL

[75] Inventors: Mitsunori Ono; Isamu Itoh; Keiji Mihayashi; Yukio Karino, all of Kanagawa, Japan

[73] Assignee: Fuji Photo Film Co., Ltd., Kanagawa, Japan

[21] Appl. No.: 574,432

[22] Filed: Jan. 27, 1984

[30] Foreign Application Priority Data

Jan. 27, 1983 [JP] Japan ................................. 58/11676

[51] Int. Cl.³ .............................................. G03C 1/02
[52] U.S. Cl. .................................... 430/566; 430/218; 430/219; 430/229; 430/505; 430/510; 430/517; 430/544; 430/596; 430/955; 430/957; 430/958; 430/959; 430/960
[58] Field of Search ............... 430/955, 956, 957, 958, 430/959, 960, 505, 566, 510, 517, 544, 596, 218, 219, 229

[56] References Cited

U.S. PATENT DOCUMENTS 3,779,753 12/1973 Bloom et al. ........................ 430/236
4,124,592 11/1978 Booom et al. ...................... 430/570

Primary Examiner—Mary F. Downey
Attorney, Agent, or Firm—Sughrue, Mion, Zinn, Macpeak and Seas

[57] ABSTRACT

A silver halide photographic light-sensitive material which comprises a light-sensitive silver halide emulsion layer having associated therewith a blocked photographic agent, said blocked photographic agent being represented by the following general formula (I):

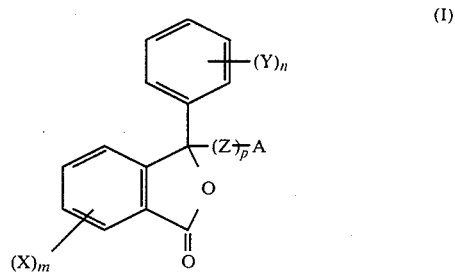

wherein A represents a photographic agent moiety which is attached to a blocking moiety through a hetero atom; Z represents a divalent linkage group; p represents 0 or 1; X and Y each represents a substituent: m represents an integer of 0 to 4: and n represents an integer of 0 to 5.

25 Claims, No Drawings

SILVER HALIDE PHOTOGRAPHIC LIGHT-SENSITIVE MATERIAL

FIELD OF THE INVENTION

The present invention relates to a silver halide photographic light-sensitive material and, more particularly, to a silver halide photographic light-sensitive material, (which is abbreviated as "photographic material" hereinafter) containing a precursor compound of a photographically useful agent in which the active group is blocked.

BACKGROUND OF THE INVENTION

Use of a photographically useful agent in such a condition that it is previously incorporated in a photographic material and so contrived that its effect will be produced at the time of necessity contains various features different from those presented by using it in a state of the addition to a processing solution. Specific examples of the features in the former case are as follows: The incorporation in a photographic material enables effective utilization of photographic agents of the kind which tend to decompose under the acid-alkaline or the oxidation-reduction condition and consequently, can not withstand the longtime storage in a processing bath and at the same time, makes it possible to simplify a composition of the processing solution to be employed associated therewith and thereby to facilitate the preparation of the processing solution. Further, this makes it possible to force a required photographic agent to function in desired time during the photographic processing or at only the desired place, that is, in only a specified layer and the neighboring layers of a multilayer photographic material. Furthermore, this permits the presence of a photographic agent in the photographic material in such an amount as to vary as a function of silver halide development. However, if a photographic agent is added to a photographic material in its active form, it becomes impossible to make the photographic agent exhibit its ability to the expected degree because during storage before the photographic processing, it reacts with other components contained in the photographic material or it is decomposed by heat, oxygen or so on. One method for solving the above-described problem involves adding a photographic agent to a photographic material in such a form that its active group is blocked and turned photographically inactive, that is, in a form of its precursor. Such a method can have various advantages in various cases to which it is applicable. For instance, in the case where the useful photographic agent is a dye, blocking a functional group of the dye which has a great effect on its spectral absorption characteristic results in a shift of is spectral absorption band to shorter wavelengths or to longer wavelengths and therefore, even if the dye is present in a silver halide emulsion layer having the spectral sensitivity in the wavelength region corresponding to the absorption band which the dye has in the unblocked state, a lowering of the sensitivity due to the so-called filter effect can be prevented. In another case where the useful photographic agent is an antifoggant or a development restrainer, blocking of their active groups makes it possible to suppress desensitization arising from adsorption of these agents to light-sensitive silver halide grains and formation of silver salts upon storage and at the same time, release of these agents at required times permits the reduction of fog density without being attended by a drop in the sensitivity, the prevention of fog due to overdevelopment, development stoppage at a desired time, and so on. In still another case where the useful photographic agent is a developer, an assistant developer or a fogging agent, if their active or adsorptive groups are blocked, various, photographically adverse effects which arise from semiquinonnes and oxidants produced by air oxidation upon storage can be prevented, and generation of fogging nuclei upon storage can also be prevented because injection of electrons into silver halide grains can be inhibited. Therefore, stable processings can be effected therein. In a further case that the useful photographic agent is a bleach accelerating agent or a bleach-fix accelerating agent, it becomes also possible to prevent reactions with other components copresent in the photographic material from occurring upon storage by blocking its active group and that, to make its expected ability bring into full play at a desired time by removing the blocking group.

As described above, a precursor of photographic agents can be utilized as an extremely valuable tool in bringing out abilities of the photographic agents to the best advantage. However, their precursor must satisfy very severe requirements for the purpose of practical use. That is, it must be one which can satisfy two requirements contradictory to each other; one consists in ensuring stable presence of the precursor under a storage condition, and the other consists in setting its blocking group loose at a desired time upon the processing and in releasing the photographic agent rapidly and that, efficiently.

A number of techniques for blocking a photographic agent have already been known. For instance, a technique using a blocking group such as an acyl group, a sulfonyl group or the like is described in published examined Japanese Patent Application No. 44806/72 (corresponding to U.S. Pat. No. 3,615,617): one which utilizes such a blocking groups as to release a photographic agent by the so-called reversal Michel's reaction is described in published examined Japanese Patent Application Nos. 39727/79 (corresponding to U.S. Pat. No. 3,674,478), 9696/80 (corresponding to U.S. Pat. No. 3,791,830) and 34927/80 (corresponding to U.S. Pat. No. 4,009,027): one which utilizes such a blocking group as to release a photographic agent with the production of quinone methide or its analogs by intramolecular electron transfer is described in published examined Japanese Patent Application Nos. 39727/79, 135944/82, 135945/82 and 136640/82: one which utilizes an intramolecular ring-closure reaction is described in published unexamined Japanese Patent Application No. 53330/80 (corresponding to U.S. Pat. Nos. 4,358,525 and 4,310,617): one which utilizes cleavage of a 5- or 6-membered ring is described in published unexamined Japanese Patent Application Nos. 76541/82 (corresponding to U.S. Pat. No. 4,335,200), 135949/82 (corresponding to U.S. Pat. No. 4,350,752) and 179842/82: and so on. However, these known techniques suffer from some defect that, for example, although stable under a storage condition, some precursor requires a high alkaline condition such as pH higher than 12 for the processing because the photographic agent-releasing rate thereof is too slow; some precursor decomposes gradually to cause a failure of its function as the precursor upon storage under moderate conditions even though it can release the photographic agent at a sufficiently fast rate by the processing under mild conditions such as in the pH range 9-11; some precursor allows little latitude in controlling the rate of releasing the photographic agent therefrom and therefore, it requires a very narrow pH range for effecting the processing; or so on.

SUMMARY OF THE INVENTION

A primary object of the present invention is, therefore, to provide a blocked photographic agent which is completely stable under storage conditions and that, release the photographic agent at a desired time upon the processing.

Another object of the present invention is to provide a blocked photographic agent which can show its function to a substantial degree over a wide pH range.

The above-described objects of the present invention are attained by a silver halide photographic light-sensitive material comprising a light-sensitive silver halide emulsion layer having associated therewith a blocked photographic agent represented by the following general formula (I):

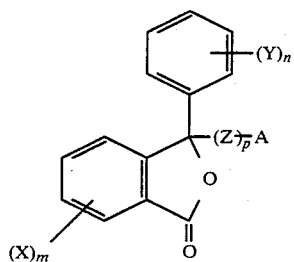

wherein A represents a photographic agent moiety which is attached to a blocking moiety through a hetero atom; Z represents a divalent linkage group; p represents 0 or 1; X and Y each represents a halogen atom, an alkyl group, an alkenyl group, an aryl group, an alkoxy group, an aryloxy group, an acyloxy group, a carboxylic acid ester group, an amino group, a carbonamido group, a sulfonamido group, an ureido group, an aminosulfonamido group, a carbamate group, a carboxy group, an alkoxycarbonyl group, an aryloxycarbonyl group, a carbamoyl group, an acyl group, a sulfo group, an alkylsulfonyl group, an arylsulfonyl group, a sulfamoyl group, a cyano group or a nitro group, and they may be the same as or different from each other; m represents an integer of 0 to 4; and n represents an integer of 0 to 5.

DETAILED DESCRIPTION OF THE INVENTION

Useful photographic agents whose monovalent residue is represented by A in the foregoing formula (I) are known ones which have at least one hetero atom such as N, S and O, and enter into combination with the blocking group through the hetero atom. Suitable examples of the photographic agent which can be employed in this invention include antifoggants and development restrainers such as mercaptotetrazoles, mercaptotriazoles, mercaptopyrimidines, mercaptobenzimidazoles, mercaptothiadiazoles, benzotriazoles, indazoles, etc.; developing agents such as p-phenylenediamines, hydroquinones, p-aminophenols, etc.; assistant developers represented by pyrazolidones; fogging agents such as hydrazines, hydrazides, etc.; silver halide solvents such as hypo, etc.; bleach accelerating agents such as aminoalkylthiols, etc.; and dyes such as azo dyes, azomethine dyes, etc.

In addition, photographic agents of the kind which further possess such a redox function as to enable the release of photographic agents as described above as a function of development, for example, color materials for color diffusion transfer films and DIR (development inhibitor releasing)-hydroquinones, can also be employed as useful photographic agents. The above-described useful photographic agents may be attached directly (when p=0 in the general formula (I)) to the 3-position of the phthalide nucleus through their hetero atom, or may be linked by the Z moiety (when p=1 in the general formula (I)) to the 3-position of the phthalide nucleus. Z represents a divalent linkage group, which is bonded to the 3-position of the phthalide nucleus through a hetero atom contained therein. The bond formed between Z and the 3-position of the phthalide nucleus is cleaved upon the processing, and the resulting $[ZA]^-$ splits per se promptly to release a photographic agent corresponding to A. Specific examples of the linkage group of the above-described kind include one which releases the agent by an intramolecular ring-closure reaction, as described in published unexamined Japanese Patent Application No. 145135/79 (corresponding to U.S. Pat. No. 4,248,962): one which releases the agent through intramolecular electron transfer, as described in British Pat. No. 2,072,363; published unexamined Japanese Patent Application No. 154234/82; and so on: one which releases the agent with the evolution of carbon dioxide, as described in published unexamined Japanese Patent Application No. 179842/82: one which releases the agent with the evolution of formaldehyde, as described in Japanese Patent Application No. 203446/82: and so on.

Structural formulae of representatives of Z are illustrated below:

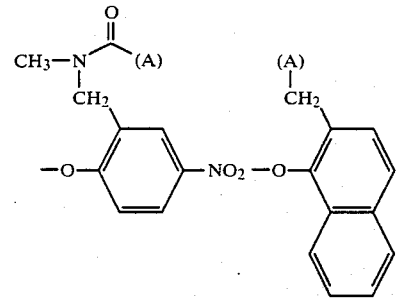

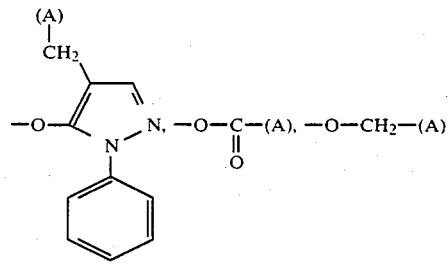

In the foregoing general formula (I), preferable examples for halogen atoms represented by X and Y include a fluorine atom, a chorine atom and a bromine atom. It is preferable that alkyl groups for X and Y have 1 to 20 carbon atoms, aryl groups therefore have 6-26 carbon atoms, alkenyl groups therefor have 2 to 26 carbon atoms, alkoxy groups therefor have 1 to 16 carbon atoms, aryloxy groups therefor have 6 to 26 carbon atoms, alkylsulfonyl groups therefor have 1 to 20 carbon atoms, and arylsulfonyl groups therefor have 6 to 26 carbon atoms. An amino group represented by X or Y may be a secondary or a tertiary amino group substituted with an alkyl group containing preferably 1 to 20 carbon atoms or an aryl group containing preferably 6 to 26 carbon atoms. An ureido group, an aminosulfonamido group, a carbamoyl group, and a sulfamoyl group may also be substituted by an alkyl group preferably having 1–20 carbon atoms or an aryl group preferably having 6–20 carbon atoms at the N-position. A carbonamido group, a sulfonamido group, a carbamate group, an alkoxycarbonyl group, an aryloxycarbonyl group and an acyl group each includes those having an alkyl group preferably containing 1 to 20 carbon atoms or an aryl group preferably containing 6 to 26 carbon atoms as a substituent. The above-described alkyl, alkenyl and aryl groups respectively include those which are further substituted by the above-described various kinds of substituents to form a substituted group having preferably up to 26 carbon atoms.

In the general formula (I) m represents desirably 0 to 2, and n represents desirably 0 to 3.

Substituents for X and Y are selected depending upon the pH of a processing solution to be employed for the processing of the photographic element in which the photographic agent precursor of the present invention is incorporated, and upon the time required for timing. For example, when a processing solution having a high pH is used, or when slow timing (usually more than 1 minute) is required, electron donating groups whose representatives are an amino group, an alkyl group, an alkoxy group and the like are selected as X and Y, whereas if fast timing (usually less than 1 minute) is required or the processing is carried out under mild alkaline conditions having pH of 9 to 11, electron attracting groups such as a halogen atom, an acyl group, sulfonyl group, cyano group and nitro group are selected as X and Y, thus achieving the desired end. In the above-described manner, it is feasible to control the releasing rate over a very wide range by choosing proper groups for X and Y. An electron attracting group and an electron donating group may also be combined in one compound represented by the general formula (I). These facts may be interpreted by the reaction scheme described below.

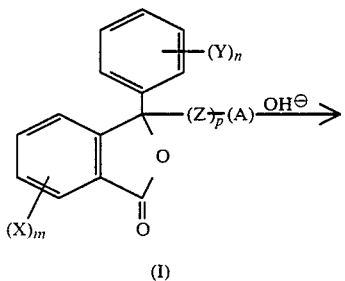

(I)

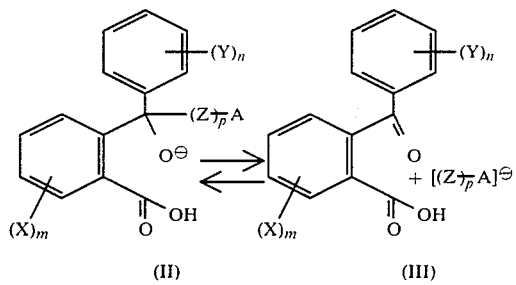

(wherein A, Z, X, Y, m, n and p have the same meanings as in the general formula (I), respectively).

The conversion from the compound of the general formula (II) produced by the reaction of the compound of the general formula (I) with an alkali into the compound of the general formula (III) with the release of $[(Z)_p\text{-}A]^-$ is a reversible reaction. In the general formula (II), the carbon atom to which the moiety $-(Z)_p\text{-}A$ is attached is located at the benzyl position of the two benzene groups which are substituted by X and Y respectively. Therefore, electronic characters of the substituents X and Y take part directly in the reversible process and have a great influence thereon. Accordingly, the rate of releasing $[(Z)_p\text{-}A]^-$ is believed to be governed predominantly by the electronic characters of two substituents X and Y. Such an effect will be understandable in the case where A is attached directly to the carbon atom situated in the above-described position (p=0) in analogy with the case where A is attached thereto through Z (p=1).

The photographic agent may also be released under heating the blocked photographic agent.

A desirable addition amount of the precursor of the present invention depends on the kind of the photographically useful agent which is the root thereof. For instance, in the case of an antifoggant or a development restrainer, a desirable addition amount of its precursor ranges from $10^{-8}$ mole to $10^{-1}$ mole per mole of silver. More specifically, in the case of the antifoggant of mercapto group-containing type it ranges from $10^{-6}$ mole to $10^{-1}$ mole per mole of silver and on the other hand, in case of the antifoggant of azole type, such as a benzotriazole, etc., it ranges from $10^{-5}$ mole to $10^{-1}$ mole per mole of silver. In the case of a developing agent, a desirable addition amount of its precursor ranges from $10^{-2}$ mole to 10 mole, particularly from 0.1 mole to 5 mole, per mole of silver. In the case of an auxiliary developer of pyrazolidone type, a suitable addition amount of its precursor ranges from $10^{-4}$ mole to 10 mole, preferably from $10^{-2}$ mole to 5 mole per mole of silver. In the case of a fogging agent, a suitable addition amount of its precursor ranges from $10^{-2}$ mole to $10^{-6}$ mole, preferably from $10^{-3}$ mole to $10^{-5}$ mole per mole of silver. In the case of a silver halide solvent such as hypo, etc., a suitable addition amount of its precursor ranges from $10^{-3}$ mole to 10 mole, preferably from $10^{-2}$ mole to 1 mole per mole of silver. In the case of a bleach accelerating agent like aminoethanethiols, etc., a suitable addition amount of its precursor ranges from $10^{-5}$ mole to 0.1 mole, preferably from $10^{-4}$ to $10^{-2}$ mole, per mole of silver. In the case of a dye or a coloring material for color diffusion transfer photography, a suitable addition amount of its precursor ranges from $10^{-3}$ mole to 1 mole, preferably from $5 \times 10^{-3}$ mole to 0.5 mole per mole of silver.

Specific examples of the precursor of the present invention are illustrated below. However, the present invention should not be construed as being limited to the following examples. (The atom marked with star is the atom through which the photographic moiety bonds to Z.)

(1) 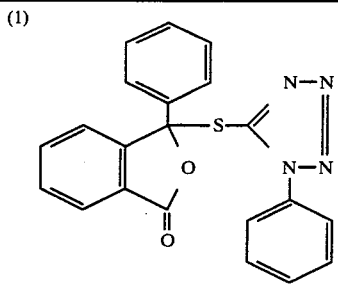  Development Restrainer
Antifoggant (2) 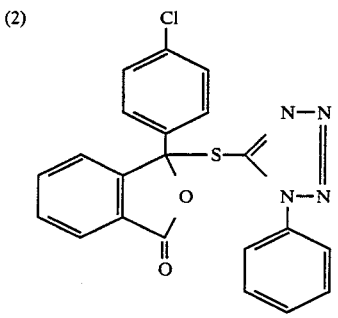  Development Restrainer
Antifoggant (3) 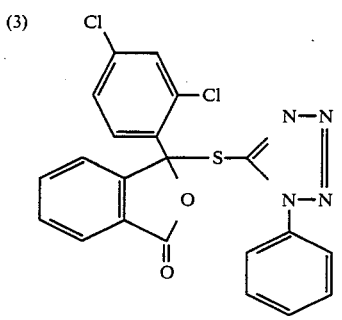  Development Restrainer
Antifoggant (4) 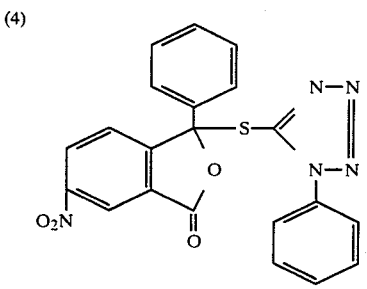  Development Restrainer
Antifoggant (5) 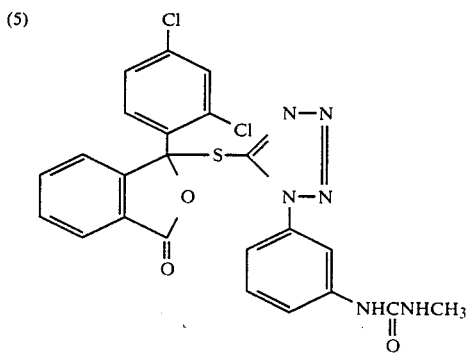  Antifoggant -continued
(6) 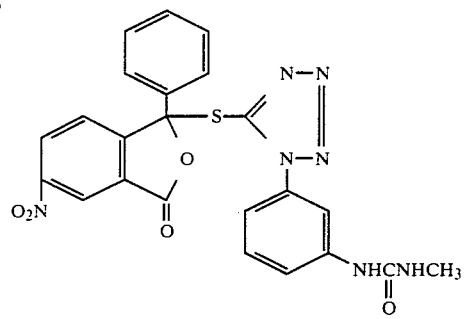 Antifoggant
(7) 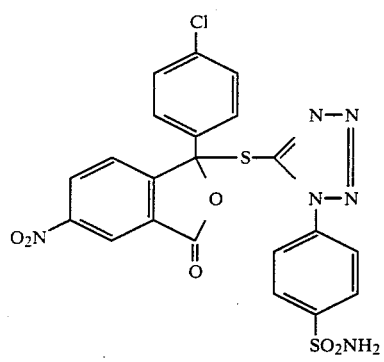 Antifoggant
(8) 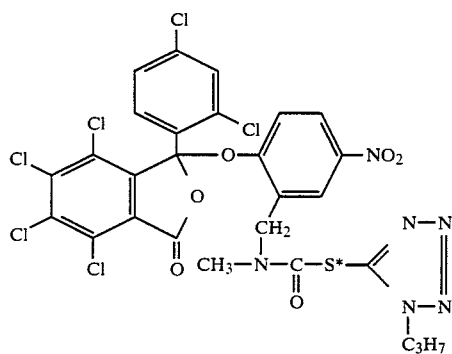 Antifoggant
(9) 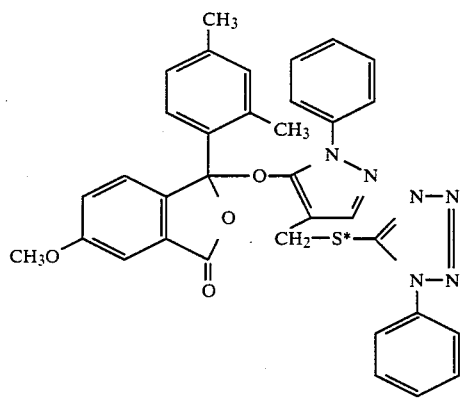 Development Restrainer
Antifoggant

(10) 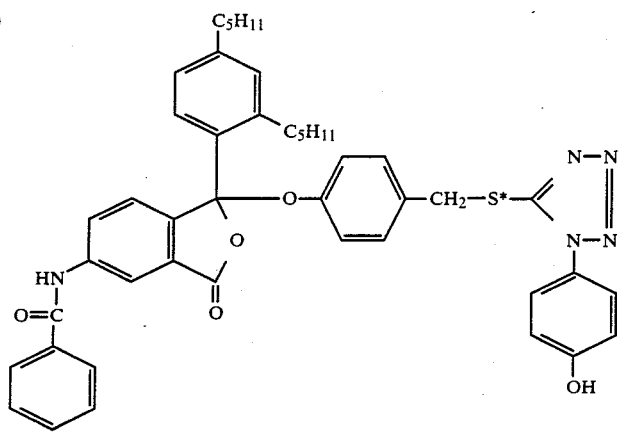 Antifoggant
(11) 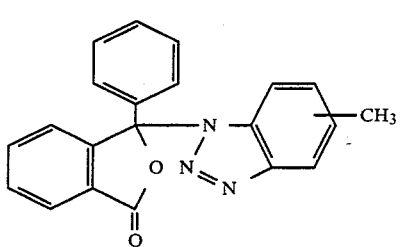 Antifoggant
(12) 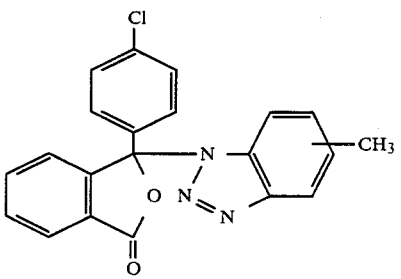 Antifoggant
(13) 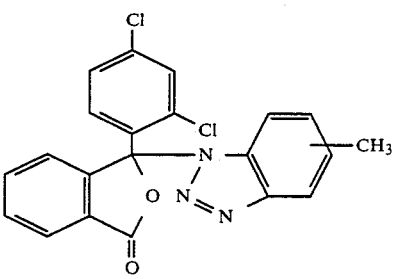 Antifoggant
(14) 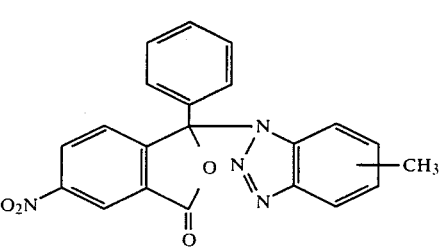 Antifoggant -continued
(15) 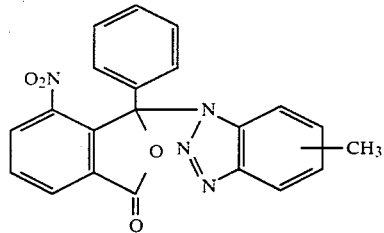 Antifoggant
(16) 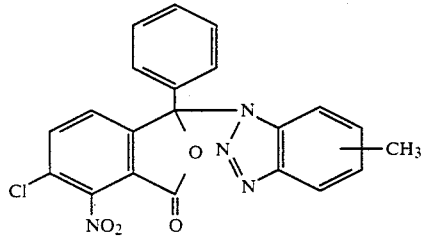 Antifoggant
(17) 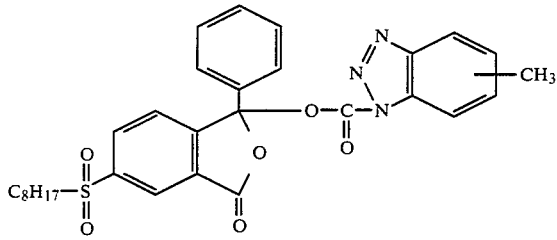 Antifoggant
(18) 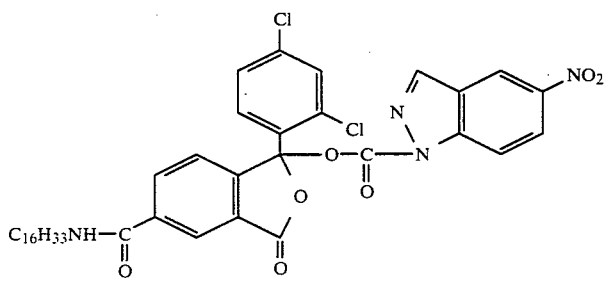 Antifoggant
(19) 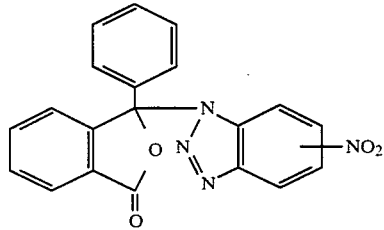 Antifoggant
(20) 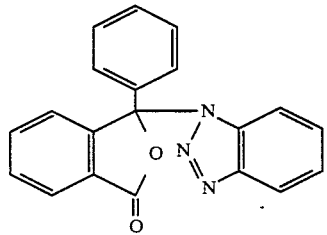 Antifoggant -continued
(21) 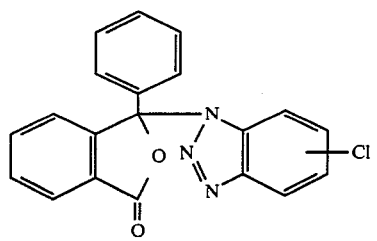 Antifoggant
(22) 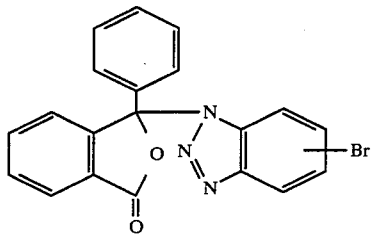 Antifoggant
(23) 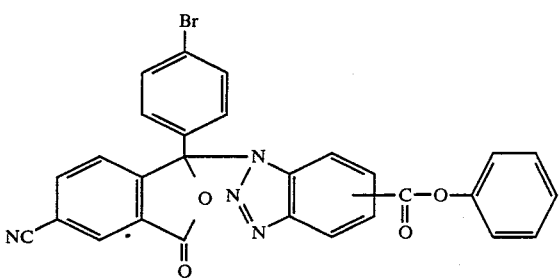 Antifoggant
(24) 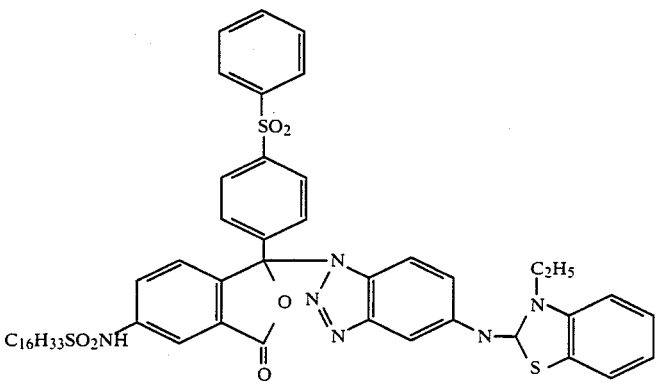 Development Restrainer Antifoggant
(25) 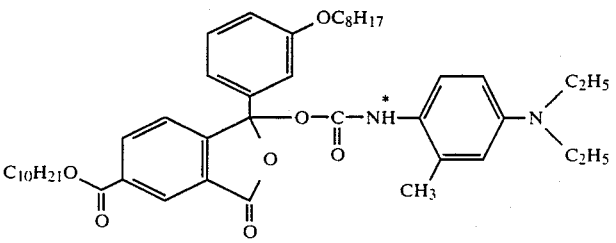 Developing Agent

(26) 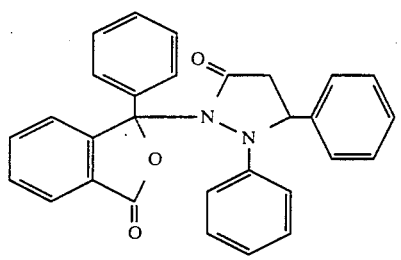 Auxiliary Developer
(27) 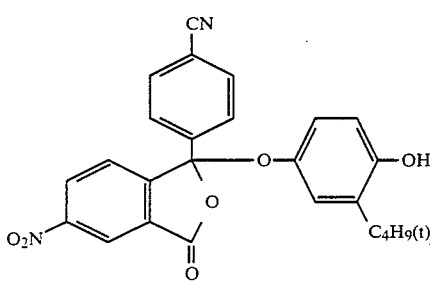 Developer
(28) 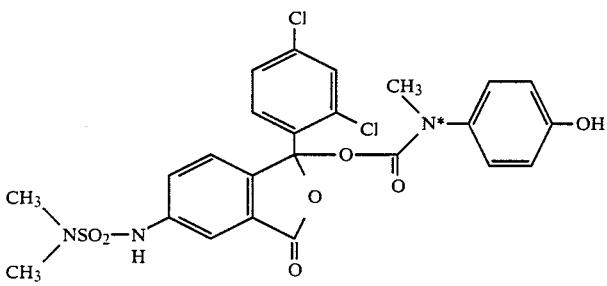 Auxiliary Developer Developing Agent
(29) 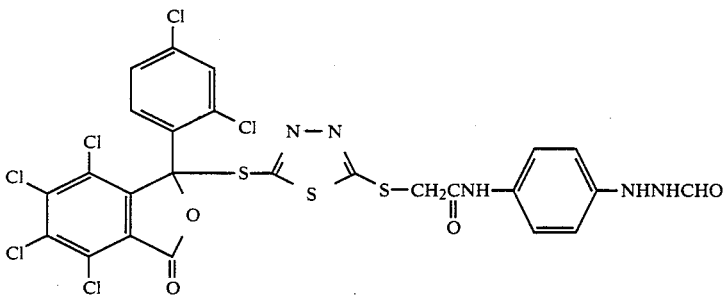 Fogging Agent
(30) 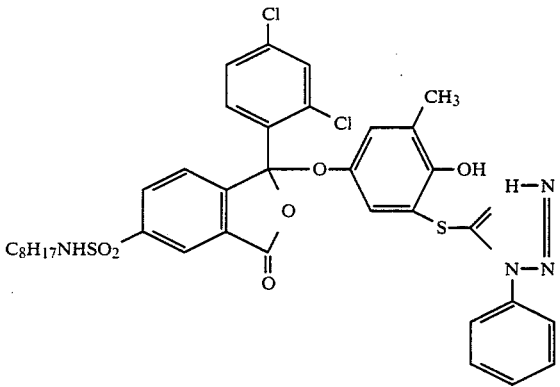 DIR-Hydroquinone

(31) 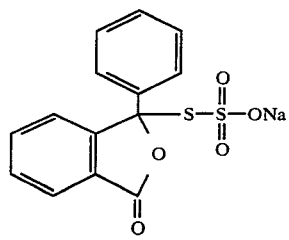 Silver Halide Solvent (Fixing Agent: Hypo)
(32) 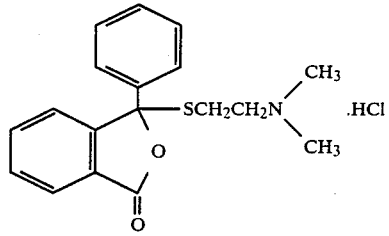 Bleach Accelerating Agent
(33) 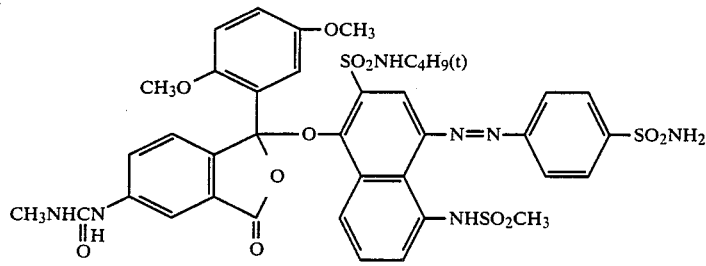 Dye (for diffusion transfer processing)
(34) 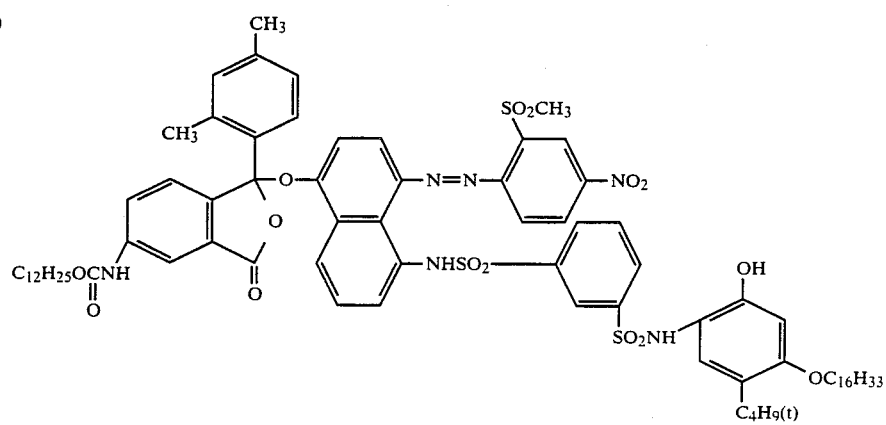 Dye (for diffusion transfer processing)
The compounds represented by the general formula (I) of the present invention are synthesized with ease using such a general method as to be traced by the following reaction scheme.

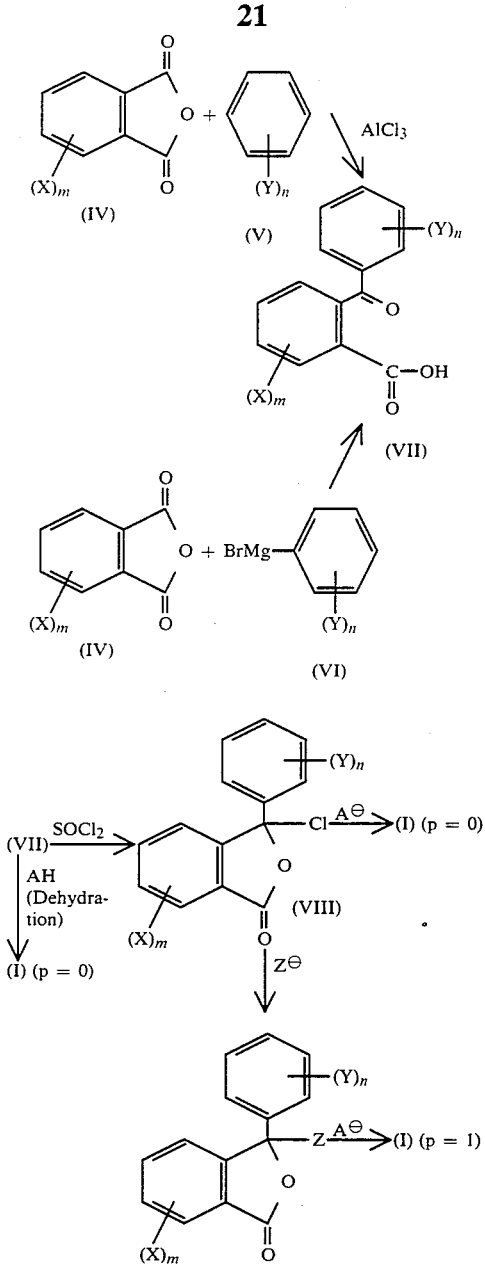

(wherein A, Z, X, Y, m, n and p have the same meanings as in the general formula (I), respectively).

That is, a ketocarboxylic acid (VII) is prepared firstly by Friedel-Crafts reaction of phthalic anhydride or its derivative (IV) with (V), or by Grignard reaction of (IV) with phenylmagnesium bromide or its derivative (IV). Then, (VII) is treated with thionyl chloride to produce the chlorinated compound (VIII), and the resulting (VIII) is allowed to react directly with an anionic form of the desired photographically useful agent (AH) to produce the intented precursor (I) (p=0). On the other hand, this precursor (I) can also be obtained by the dehydrating condensation reaction of (VII) with the desired photographically useful agent. As for the precursor (I) into which a linkage group Z is introduced (p=1), it can be prepared according to the method described in, e.g., published unexamined Japanese Patent Application 145135/79, etc., in which the Z group is firstly introduced in the compound (VIII) and then, the resulting compound is allowed to react with $A^{\ominus}$.

Typical synthesis examples of the compound represented by the general formula (I) of the present invention are illustrated in detail below.

Synthesis Example 1

Synthesis of Compound (1)

Synthesis of 3-Chloro-3-Phenylphthalide;

To 25 ml of thionyl chloride was added 23 g of commercial 2-benzoylbenzoic acid. It was heated with stirring for 3 hours on an oil bath whose temperature was maintained at 50°–60° C. Excess thionyl chloride was distilled away under reduced pressure, and the thus obtained brown syrupy material was distilled under reduced pressure to obtain the intended compound as a fraction of b.p. of 175°–178°/3 mmHg.

Synthesis of Compound (1):

To 300 ml of dried dimethylformamide, was added 14.56 g (0.12 mol.) of potassium tert-butoxide and 18 g (0.1 mol.) of 1-phenyl-5-mercaptotetrazole. The mixture was stirred for 20 minutes at room temperature. Thereafter, to the mixture cooled to 5° C. and kept there, was gradually added dropwise a solution prepared by adding 25 g (0.1 mol.) of 3-chloro-3-phenylphthalide to 75 ml of dried dimethylformamide. At the conclusion of the dropwise addition, the cooling bath was removed, and the mixture was stirred for 2 hours at room temperature. Thereto, 300 ml of a saturated aqueous solution of ammonium chloride was added. The reaction mixture was extracted with ethyl acetate repeatedly. The extract was washed with water, and the resulting organic layer was dried over anhydrous sodium sulfate. Sodium sulfate was filtered off with suction, and the filtrate was concentrated to yield 35 g of oily substance. This oily substance was separated and purified by flash column chromatography (silica gel: 700 g, eluate: hexane-ethyl acetate (3:1 by vol.) mixture). Thus, the intended compound, 3-phenyl-3-(1-phenyltetrazole-5-ylthio)phthalide (1), was obtained in the form of white crystals. Yield 21.5 g, Melting Point 137°–139° C.

In analogy with the above-described Compound (1), Compound (31) and Compound (32) were obtained by reacting 3-chloro-3-phenylphthalide with the sodium or potassium salts of mercapto compounds corresponding to group A in the Compounds (31) and (32), respectively.

Sodium 3-phenyl-3-sulfothiophthalide (Compound (31)), Decomposition Point 220° C.

3-(2-Dimethylaminoethylthio)-3-phenylphthalide hydrochloride (Compound (32)), Melting Point 123°–125° C.

Synthesis Example 2

Synthesis of Compound (2)

Synthesis of 2-(4-Chlorobenzoyl)benzoic acid:

To a solution prepared by adding 30 g (0.2 mol.) of phthalic anhydride to 122 ml of dried chlorobenzene, was added 64 g (0.48 mol.) of well-ground anhydrous aluminium chloride with stirring. The reaction temperature rose gradually, and the reaction system reached a refluxing condition. The refluxing was continued for 1 hour as the reaction temperature was controlled so that the reaction system refluxed moderately using the ice bath. Then, the reaction product solidified spontaneously. 300 ml of water was added dropwise to the reaction system while cooling by means of an ice bath. The thus produced white precipitate was thoroughly washed with water and cooled ethanol to obtain 45 g of crude crystals. These crude crystals were recrystallized from benzene to obtain the intended compound. Yield 38 g, Melting Point 146° to 148° C.

Synthesis of 3-Chloro-3-(4-chlorophenyl)phthalide:

To 25 ml of thionyl chloride was added 26 g of 2-(4-chlorobenzoyl)benzoic acid. The mixture was heated with stirring for 3 hours on the oil bath kept at a temperature of 60° C. Excess thionyl chloride was distilled away under reduced pressure, and the marked compound was obtained as a yellow oily substance. This substance was unstable and therefore, it was submitted to the next reaction without being purified. Yield 27 g.

Synthesis of Compound (2):

To 200 ml of dried dimethylforamide, was added 2.24 g (0.02 mol.) of potassium tert-butoxide and 3.2 g (0.018 mol.) of 1-phenyl-5-mercaptotetrazole. The mixture was stirred for 15 minutes at room temperature. Thereafter, to the mixture which was cooled to 5° C. and kept there, was gradually added dropwise a solution containing 5.0 g (0.018 mol.) of 3-chloro-3-(4-chlorophenyl)phthalide in 50 ml of dried dimethylformamide. After dropwise addition, the stirring was continued for 4 hours at room temperature. Thereto, 200 ml of a saturated aqueous solution of ammonium chloride was added. The reaction mixture was extracted with ethyl acetate repeatedly. The extract was washed with water, and the resulting organic layer was dried over anhydrous sodium sulfate. Sodium sulfate was filtered off with suction, and the filtrate was concentrated to yield 7.5 g of syrupy material. This syrupy material was separated and purified by flash column chromatography (silica gel: 400 g, eluate: ethyl acetate-hexane (1:3 by volume) mixture). Thus, the intended compound, 3-(1-phenyltetrazole-5-ylthio)-3-(4-chlorophenyl)phthalide (2), was obtained in a form of white crystals. Yield 5.2 g, Melting Point 133°–135° C.

Synthesis Example 3

Synthesis of Compound (3)

Synthesis of 2-(2,4-Dichlorobenzoyl)benzoic Acid:

To a solution prepared by adding 30 g (0.2 mol.) of phthalic anhydride to 146 g (1.0 mol.) of dried 1,3-dichlorobenzene, was added 64 g (0.48 mol.) of well-ground anhydrous aluminium chloride with stirring. The mixture was heated and stirred for 3 hours on the oil bath kept at 120° C. Thereafter, the reaction mixture was sufficiently cooled on an ice bath and thereto, 100 ml of water was added dropwise. The thus produced white precipitate was thoroughly washed with successive, water and cooled ethanol to obtain 32 g of crude crystals. These crude crystals were recrystallized from benzene to obtain the marked compound. Yield 24 g, Melting Point 178° to 181° C.

Synthesis of 3-Chloro-3-(2,4-dichlorophenyl)phthalide:

To 25 ml of thionyl chloride was added 30 g of 2-(2-4-dichlorobenzoyl)benzoic acid. The mixture was heated with stirring for 3 hours on the oil bath kept at a temperature of 50°–60°. Excess thionyl chloride was distilled away under reduced pressure, and the intended compound was obtained as a brown solid. This solid was unstable and therefore, it was submitted to the next reaction without receiving any purification treatment. Yield 29.2 g.

Synthesis of Compound (3):

To 300 ml of dried dimethylformamide, was added 5.6 g (0.05 mol.) of potassium tert-butoxide and 8.9 g (0.05 mol.) of 1-phenyl-5-mercaptotetrazole. The mixture was stirred for 20 minutes at room temperature. Thereafter, to the mixture which was cooled to 5° C. and kept there, was added gradually dropwise a solution prepared by adding 13 g (0.04 mol.) of 3-chloro-3-(2,4-dichlorophenyl)phthalide in 75 ml of dried dimethylformamide. After dropwise addition, the cooling bath was removed, and the mixture was stirred for 5 hours at room temperature. Thereto, 300 ml of a saturated aqueous solution of ammonium chloride was added. The reaction mixture was extracted with ethyl acetate repeatedly. The extract was washed with water, and the resulting organic layer was dried over anhydrous sodium sulfate. Sodium sulfate was filtered off with suction, and the filtrate was concentrated to yield 23.5 g of oily substance. This oily substance was separated and purified by flash column chromatography (silica gel: 800 g, eluate: hexane-ethyl acetate (3:1 by volume) mixture). Thus, the intended compound, 3-(1-phenyl-tetrazole-5-ylthio)-3-(2,4-dichlorophenyl)phthalide (3), was obtained in a form of white crystals. Yield 7.8 g, Melting Point 148° to 149° C.

Synthesis Example 4

Synthesis of Compound (4)

Synthesis of 2-Benzoyl-5-nitrobenzoic Acid:

50 g (0.26 mol.) of 4-nitro-phthalic anhydride was dissolved in 400 ml of dried tetrahydrofuran. The solution was cooled to 5° C. and thereto with stirring, 260 ml of a tetrahydrofuran solution of phenylmagnesium bromide (0.26 mol.), which had been prepared separately, was gradually added dropwise taking about 40 minutes. After the dropwise addition, the stirring was continued for an additional 6 hours at 5° C. in a stream of nitrogen. Then, the cooling bath was removed, and the reaction mixture was allowed to stand overnight. Then, tetrahydrofuran was distilled away under reduced pressure, and 450 ml of a saturated aqueous solution of ammonium chloride was added and further, 100 ml of 6N hydrochloric acid was added. The resulting reaction mixture was extracted with ethyl acetate repeatedly. After washing the extract with water, the organic layer was dried over anhydrous sodium sulfate. Thereafter, sodium sulfate was filtered off with suction, and the filtrate was concentrated to obtain about 60 g of brown syrupy material. A 60 g portion of this syrupy material was purified by flash column chromatography (silica gel: 1 L Kg, eluate: ethyl acetate) to obtain 31 g of crude crystals. They were recrystallized from ethanol to obtain the intended compound. Yield 27 g, Melting Point 214° to 216° C.

Synthesis of Compound (4):

To 20 ml of thionyl chloride was added 25 g of 2-benzoyl-5-nitrobenzoic acid. The mixture was heated and stirred for 3 hours on the oil bath kept at a temperature of 60° C. Excess thionyl chloride was distilled away under reduced pressure, and 27.5 g of 3-chloro-4-phenyl-6-nitrophthalide was obtained as a brown oily substance. Separately, 4.48 g (0.04 mol.) of potassium tert-butoxide and 5.34 g (0.03 mol.) of 1-phenyl-5-mercaptotetrazole were added to 200 ml of dried dimethylformamide, and stirred for 20 minutes at room temperature. The resulting mixture was cooled to 5° C. and thereto, was added dropwise gradually the previously prepared solution containing 9.0 g (0.03 mol.) of 3- chloro-3-phenyl 6-nitrophthalide in 75 ml of dried dimethylformamide as the mixture was maintained at 5° C. After the conclusion of the dropwise addition, the reaction mixture was stirred for 30 minutes at 5° C. and further, for 2 hours at room temperature. Thereto, 200 ml of a saturated aqueous solution of ammonium chloride was added. The reaction mixture was extracted with ethyl acetate repeatedly. The extract was washed with water, and the resulting organic layer was dried over anhydrous sodium sulfate. Sodium sulfate was filtered off with suction, and the filtrate was concentrated to yield 9.2 g of crude crystals. These crude crystals were separated and purified by flash column chromatography (silica gel: 400 g, eluate: hexane-ethyl acetate (3:1 by volume) mixture). Thus, the intended compound, 3-(1-phenyltetrazole-5-ylthio)-3-phenyl-6-nitrophthalide (4), was obtained. It was recrystallized from an ethyl acetate-hexane mixture. Yield 5.5 g, Melting Point 176° to 179° C.

Synthesis Example 5

Synthesis of Compound (6)

To 80 ml of dried dimethylformamide, were added 0.80 g (0.0071 mol.) of potassium tert-butoxide and 1.73 g (0.0069 mol.) of 1-[3-(3-methylureido)phenyl]-5-mercaptotetrazole. The mixture was stirred for 10 minutes at room temperature and then, it was cooled to 5° C. Thereto, 2 g (0.0069 mol.) of 3-chloro-3-phenyl-6-nitrophthalide, which had been synthesized in the manner described in Synthesis Example 4, in 20 ml of dried dimethylformamide was gradually added dropwise as the mixture was maintained at 5° C. At the conclusion of the dropwise addition, the cooling bath was removed, and the mixture was stirred for 4 hours at room temperature. Thereto, 100 ml of a saturated aqueous solution of ammonium chloride was added. The reaction mixture was extracted with ethyl acetate repeatedly, and the extract was washed with water. The resulting organic layer was dried over anhydrous sodium sulfate, and the sodium sulfate was filtered off with suction. The filtrate was concentrated to obtain 4.2 g of brown oily substance, and the oily substance was separated and purified by flash column chromatography (silica gel: 200 g, eluate: ethyl acetate-hexane (4:1 by volume) mixture) to obtain the intended compound 3-{1-[3-(3-methylureido)phenyl]-5-mercaptotetrazolythio}-3-phenyl-6-nitrophthalide (6). Yield 1.8 g, Melting Point 198° C. or higher (decomposed).

Synthesis Example 6

Synthesis of Compound (15)

Synthesis of 2-benzoyl-3-nitrobenzoic acid:

In 300 ml of dried tetrahydrofuran, was dissolved 30 g (0.155 mol.) of 3-nitrophthalic anhydride. The solution was cooled to 5° C. and thereto with stirring, 80 ml of a tetrahydrofuran solution containing 0.155 mol. of phenylmagnesium bromide prepared separately was added dropwise gradually taking about 30 minutes. After the dropwise addition, the stirring was continued for an additional 6 hours at 5° C. in a stream of nitrogen. Then, the cooling bath was removed, and the reaction mixture was allowed to stand overnight. Then, tetrahydrofuran was distilled away under reduced pressure, and 300 ml of a saturated aqueous solution of ammonium chloride was added and then, 50 ml of 6N hydrochloric acid was further added to the reaction mixture. The thus obtained reaction product was extracted with ethyl acetate repeatedly, and washed with water. The resulting organic layer was dried over anhydrous sodium sulfate, and the sodium sulfate was filtered off with suction. The filtrate was concentrated to obtain 42 g of brown oily substance. This oily substance was separated and purified by flash column chromatography (silica gel: 1 Kg, eluate: ethyl acetate) to yield 23 g of crude crystals. The crude crystals were recrystallized from acetic acid to obtain the intended compound. Yield 18 g, Melting Point 238° to 239° C.

Synthesis of Compound (15):

To 37 ml of thionyl chloride was added 40 g of 2-benzoyl-3-nitrobenzoic acid. The mixture was heated and stirred for 4 hours on an oil bath kept at a temperature of 50° to 60° C. Excess thionyl chloride was distilled away under reduced pressure, and 40.2 g of 3-chloro-3-phenyl-4-nitrophthalide was obtained as a brown oily substance. Separately, 9.0 g (0.08 mol.) of potassium tert-butoxide and 9.3 g (0.07 mol.) of 5-methylbenzotriazole were added to 300 ml of dried dimethylformamide, and stirred for 20 minutes at room temperature. The resulting mixture was cooled to 5° C. and thereto, was added dropwise gradually the previously prepared solution containing 20 g (0.07 mol.) of 3-chloro-3-phenyl-4-nitrophthalide in 100 ml of dried dimethylformamide as the mixture was kept at 5° C. After the dropwise addition, the cooling bath was removed, and the stirring was further continued for 5 hours at room temperature. Thereto, 300 ml of a saturated aqueous solution of ammonium chloride was added subsequently. The reaction mixture was extracted with ethyl acetate repeatedly, and the extract was washed with water. The rsulting organic layer was dried over anhydrous sodium sulfate, and the sodium sulfate was filtered off with suction. The filtrate was concentrated to obtain 27.5 g of oily substance. This oily substance was separated and purified by flash column chromatography (silica gel: 1 Kg, eluate: hexane-ethyl acetate (2:1 by volume) mixture) to obtain the intended compound, 3-phenyl-3-(5-methyl-1-benzotriazolyl)-4-nitrophthalide, in the form of white crystals. Yield 6.9 g, Melting Point 240° to 248° C.

In analogy with the synthesis of the above-described Compound (15), other substituted benzotriazoles can also be synthesized by reacting corresponding chlorophthalides with corresponding benzotriazoles. Melting points of some of the substituted benzotriazoles prepared in such a manner are described below.

3-Phenyl-3-(5-methyl-1-benzotriazolyl)phthalide (Compound (11)) Melting Point 179° to 182° C.

3-Phenyl-3-(5-chloro-1-benzotriazolyl)phthalide (Compound (21)) Melting Point 79° to 82° C.

3-Phenyl-3-(5-nitro-1-benzotriazolyl)phthalide (Compound (19)) Melting Point 83° to 85° C.

3-Phenyl-3-(5-methyl-1-benzotriazolyl)-6-nitrophthalide (Compound (14)) (Amorphous).

3-(4-Chlorophenyl)-3-(5-methyl-1-benzotriazolyl)phthalide (Compound (12)) Melting Point 188° to 194° C.

3-(2,4-Dichlorophenyl)-3-(5-methyl-1-benzotriazolyl)phthalide (Compound (13)) Melting Point 220° to 227° C.

3-Phenyl-3-(5-methyl-1-benzotriazolyl)-6-chloro-7-nitrophthalide (Compound (16)) Melting Point 189° to 190° C.

Synthesis Example 7

Synthesis of Compound (22)

10.0 g (0.04 mol.) of commercial 2-benzoylbenzoic acid and 7.8 g (0.04 mol.) of 5-bromobenzotriazole were added to 300 ml of dried xylene, and refluxed for 8 hours as heat was applied thereto by means of the dehydration-reflexing apparatus. After cooling, the insoluble material was filtered off with suction, and the filtrate was concentrated to obtain 12.4 g of oily substance. This oily substance was separated and purified by flash column chromatography (silica gel: 400 g, eluate: hexane-ethyl acetate (3:2 by volume) mixture) to obtain the intended compound, 3-phenyl-3-(5-bromo-1-benzotriazolyl)phthalide (22), in the form of white crystals. Yield 8.1 g, Melting Point 128° to 131° C.

Compound (20) and Compound (26) can be synthesized in the same manner as in the synthesis of Compound (22).

3-Phenyl-3-(1-benzotriazolyl)phthalide (Compound (20) Melting Point 174° to 176° C.

3-(1,5-Diphenyl-3-keto-2-pyrazolidinyl)-3-phenylphthalide (Compound (26)) Melting Point 115° to 118° C.

The precursors of the present invention may be used in combination with two or more thereof.

It is preferable that the blocked photographic agent contains group Z, especially when the photographic agent which is released has a high tendency to be adsorbed to silver halide grains and when a long transferring distance are required. When Z is contained in a blocked photographic agent the released substance effectively transfers as $[Z-A]^-$. For example, when a blocked antifoggant such as that having a mercapto group or being a triazole derivative is used in a layer of a photographic material, and it is required that the released antifoggant acts also in another layer to obtain an antifogging effect, a blocked antifoggant having group Z is preferably used.

The blocked photographic agents (precursors) of the present invention may be added to any constituent layers of a silver halide photographic material including a silver halide emulsion layer, a coloring material layer, a subbing layer, a protective layer, an interlayer, a filter layer, an antihalation layer, an image-receiving layer, a cover sheet layer and other auxiliary layers.

Incorporation of the precursors of the present invention into the above-described layers can be carried out by adding them to coating compositions for forming such layers as they are, or in such a state that they are dissolved in a proper concentration in such a solvent as not to affect adversely the photographic material, such as water, alcohol or the like. Also, the precursors can be added in such a state that they are firstly dissolved in a high boiling point solvent and/or a low boiling point solvent and then, emulsified and dispersed in an aqueous solution. Moreover, they may be added in such a state that they are made to soak into polymer latexes using the methods as described in published unexamined Japanese Patent Applications Nos. 39853/76, 59942/76 and 32552/79; U.S. Pat. No. 4,199,363; and so on.

The precursors may be added at any stages of the preparation process of the photographic material. However, it is generally preferable to choose the stage of just before the coating.

The compounds of the present invention can be employed for, e.g., color photographic materials of the coupler type.

A general method for forming color images using a color photographic material consists of developing a silver halide light-sensitive material with an aromatic primary amine developing agent in the presence of color couplers, which have such an ability as to form dyes by reacting with the oxidation products of developing agents, to produce azomethine dyes or indoaniline dyes. The basis of the above-described color development method is invented by L. D. Mannes & L. Godowsky in 1935 and thereafter, various improvements have been introduced thereinto. Nowadays, this color development method is universally employed in this art.

In this method, the substractive color process is usually employed for color reproduction, wherein silver halide emulsions which are sensitive selectively to blue, green and red lights respectively, and yellow, magenta and cyan color image-forming agents which bear their respective complementary relations to those lights are used. In order to form yellow color image, couplers of, e.g., acylacetoanilide type or dibenzoylmethane type are used. In order to form magenta color image, couplers of pyrazolone type, pyrazolobenzimidazole type, cyanoacetophenone type or indazolone type are predominantly used. In order to form cyan color image, couplers of phenol type, e.g., phenols and naphthols, are predominantly used.

In general, color photographic materials are divided broadly into two main groups; one group consists of the coupler-in-developer type, which utilize couplers added to a developing solution, and the other group consists of those of the coupler-in-emulsion type, which contain couplers in their light-sensitive layers in such a state that the couplers may retain their own functions independently. In the latter materials, dye image-forming couplers are incorporated in silver halide emulsion layers. For couplers to be added to emulsion layers, it is necessary to be rendered nondiffusible (to have diffusion resistance) in the matrix of emulsion binder.

The processing steps of color photographic materials of the coupler-in-emulsion type comprises basically of the following three steps.

(1) Color developing step
(2) Bleaching step
(3) Fixing step

A bleaching step and a fixing step may be carried out at the same time. That is, it is called a bleach-fix (blix) step, and both developed silver and undeveloped silver halide are desilvered in this step. Besides involving the abovedescribed two basic steps, color developing and desilvering ones, the actual processing for development includes auxiliary steps for the purposes of retaining photographic and physical qualities of the image, improving the storability of the image, and so on. For instance, there are steps using a hardening bath for preventing light-sensitive films from being excessively softened during the processing, a stop bath for stopping a development reaction effectively, an image-stabilizing bath, a delaminating bath for removing a backing layer from the support, and so on.

Couplers are added to or dispersed into gelatinsilver halide emulsions or hydrophilic colloid according to conventionally known methods. Specifically, a method of dispersing a coupler in the form of a mixture with a high boiling point organic solvent such as dibutyl phthalate, tricresyl phosphate, waxes, a higher fatty acid or its ester, etc.; such a method as described in U.S. Pat. Nos. 2,304,939 and 2,322,027, and so on; a method of dispersing a coupler in the form of a blend with a low boiling point organic solvent or a water soluble organic solvent; a method of dispersing a coupler in the form of a mixture with a combination of a high boiling point and a low boiling point organic solvents; such a method as described in, e.g., U.S. Pat. Nos. 2,801,170, 2,801,171 and 2,949,360, and so on; a method of dispersing a coupler by itself or in combination with other couplers required for combined use, such as a colored coupler and an uncolored coupler, in case that the coupler has a low melting point (e.g., not higher than 75° C.): such a method as described in German Pat. No. 1,143,707) and so on can be employed.

Suitable examples of a dispersing aid which can be employed for dispersion of couplers include anionic surface active agents (e.g., sodium alkylbenzenesulfonates, sodium dioctylsulfosuccinate, sodium dodecylsulfate, sodium alkylnaphthalenesulfonates, Fischer type couplers, etc.), amphoteric surface active agents (e.g., N-tetradecyl-N,N-dipolyethylene-α-betaine) and non-ionic surface active agents (e.g., sorbitan monolaurate, etc.).

Suitable couplers which can be used in combination with the compounds of the present invention include known couplers as set forth below.

Specific examples of magenta color-forming couplers which can be used include those described in U.S. Pat. Nos. 2,600,788; 2,983,608; 3,062,653; 3,127,269; 3,311,476; 3,419,391; 3,519,429; 3,558,319; 3,582,322; 3,615,506; 3,834,908 and 3,891,445: West German Pat. No. 1,810,464: West German Patent Application (OLS) Nos. 2,408,665; 2,417,945; 2,418,959 and 2,424,467: published examined Japanese Patent Application No. 6031/65, published unexamined Japanese Patent Application Nos. 20826/76, 58922/77, 129538/74, 74027/74, 159336/75, 42121/77, 74028/74, 60233/75, 26541/76 and 55122/78, and so on.

Specific examples of yellow color-forming couplers which can be used include those described in U.S. Pat. Nos. 2,875,057; 3,265,506; 3,408,194; 3,551,155; 3,582,322; 3,725,072 and 3,891,445: West German Pat. No. 1,547,868: West German Patent Applications (OLS) Nos. 2,219,917; 2,261,361; and 2,414,006: British Pat. No. 1,425,020: published examined Japanese Patent Application No. 10783/76: published unexamined Japanese Patent Applications Nos. 26133/72, 73147/73, 102636/76, 6341/75, 123342/75, 130442/75, 21827/76, 87650/75, 82424/77 and 115219/77: and so on.

Specific examples of cyan color-forming couplers which can be used include those described in U.S. Pat. Nos. 2,369,929; 2,434,272; 2,474,293; 2,521,908; 2,895,826; 3,034,892; 3,311,476; 3,458,315; 3,476,563; 3,583,971; 3,591,383; 3,767,411 and 4,004,929: West German Patent Applications (OLS) Nos. 2,414,830 and 2,454,329: published unexamined Japanese Patent Applications Nos. 59838/73, 26034/76, 5055/73, 146828/76, 69624/77 and 90932/77: and so on.

Specific examples of colored couplers which can be used include those described in U.S. Pat. Nos. 3,476,560; 2,521,908 and 3,034,892; published examined Japanese Patent Applications Nos. 2016/69, 22335/63, 11304/67 and 32461/69: published unexamined Japanese Patent Applications Nos. 26034/76 and 42121/77: and West German Patent Application (OLS) No. 2,418,959.

Specific examples of DIR couplers which can be used include those described in U.S. Pat. Nos. 3,227,554; 3,617,291; 3,701,783; 3,790,384 and 3,632,345: West German Patent Applications (OLS) Nos. 2,414,006; 2,454,301 and 2,454,329: British Pat. No. 953,454: published unexamined Japanese Patent Applications Nos. 69624/77 and 122335/74: and published examined Japanese Patent Application No. 16141/76.

In addition to DIR couplers, compounds capable of releasing a development inhibitor with the progress of development may be incorporated in a photosensitive material. For example, compounds as described in U.S. Pat. Nos. 3,297,445 and 3,379,529: West German Patent Application (OLS) No. 2,417,914: published unexamined Japanese Patent Applications Nos. 15271/77 and 9116/78: and so on can be used.

Suitable high boiling point organic solvents which can be used are those described in U.S. Pat. Nos. 2,322,027; 2,533,514 and 2,835,579: published examined Japanese Patent Application No. 23233/71: U.S. Pat. No. 3,287,134: British Pat. No. 958,441: published unexamined Japanese Patent Application No. 1031/72: British Pat. No. 1,222,753: U.S. Pat. No. 3,936,303: published unexamined Japanese Patent Applications Nos. 26037/76 and 82078/75: U.S. Pat. Nos. 2,353,262; 2,852,383; 3,554,755; 3,676,137; 3,676,142; 3,700,454; 3,748,141 and 3,837,863: West German Patent Application (OLS) No. 2,538,889: published unexamined Japanese Patent Applications Nos. 27921/76, 27922/76, 26035/76, 26036/76 and 62632/75: published examined Japanese Patent Application No. 29461/74: U.S. Pat. No. 3,936,303 and 3,748,141: published unexamined Japanese Patent Application No. 1521/78: and so on.

Upon the application to the color diffusion transfer photographic process, the photographic element of the present invention may constitute any type of film unit, including the peel-apart type, the integrated type as described in published examined Japanese Patent Applications Nos. 16356/71 and 33697/73; published unexamined Japanese Patent Application No. 13040/75; and British Pat. No. 1,330,524; or the peel-apart unneeded type as described in published unexamined Japanese Patent Application No. 119345/82.

The conventional color diffusion transfer silver halide photographic light-sensitive material, to which the present invention can be applied, comprises (1) a light-sensitive element comprising a support having thereon at least one light sensitive silver halide emulsion layer of the present invention having associated therewith a dye image-providing material, and (2) an image receiving element wherein a diffusible dye produced in an imagewise manner from the dye image-providing material is fixed to form an image. If desired, the element may have further layers or material such as at least one hydrophilic colloidal layer other than said silver halide emulsion layer, an alkaline processing composition with which the light-sensitive silver halide emulsion which is imagewise exposed is developable, and a neutralizing function for neutralizing the alkaline processing composition.

A specific example for the above described material comprises (1) a light-sensitive sheet comprising a transparent support having thereon (i) an image receiving element which enables fixation of diffusible dyes to form an image, (ii) a light-reflecting white layer, a light intercepting layer, and (iii) at least one silver halide emulsion layer having associated therewith a dye image-providing material, (2) an alkaline processing composition which enables the development of said light-sensitive element after imagewise exposure, (3) and a cover sheet comprising a support having thereon a layer having a neutralizing function for neutralizing said alkaline processing composition.

In any film units of the above-described formats, it is advantageous to provide a polymeric acid layer protected by a neutralization timing layer from the standpoint of extending a latitude in the processing temperature.

The precursors represented by the foregoing formula (I) may be added to any layers of the film unit of the diffusion transfer photographic material, provided that they are associated with silver halide emulsions so as to act effectively upon the development of the silver halide emulsions. However, it is preferable to add them to light-sensitive layers such as silver halide emulsion-containing layers, dye image providing compound-containing layers, or other auxiliary layers such as an inter layer; an imagereceiving layer or a white reflecting layer; or a neutralizing structure such as a neutralizing layer, a neutralization timing layer or the like. Among these layers, the neutralizing layer or the neutralization timing layer is especially desirable for their addition.

In the present invention, internal latent image type silver halide emulsions can be used to advantage. Suitable examples of the emulsions of this kind include conversion type emulsions, core-shell type emulsions and emulsions with a built-in foreign metal, which are described in, e.g., U.S. Pat. Nos. 2,592,250; 3,206,313; 3,447,927; 3,761,276 and 3,935,014; and so on.

Suitable examples of a negative dye image-providing compound which is useful in the present invention include couplers capable of forming or releasing dyes by reacting with oxidized color developing agents, with specific examples including those described in U.S. Pat. No. 3,227,550; Canadian Pat. No. 602,607; and so on.

More preferable negative dye image-providing compounds are dye releasing redox compounds which can release dyes by reaction with developers present in an oxidized condition or with electron transfer agents. The representatives of such compounds are described in, e.g., published unexamined Japanese Patent Applications Nos. 33826/73, 54021/79, 113624/76 and 71072/81; and so on. On the other hand, suitable examples of immobile, positive dye image-providing agents which can be used in the present invention include compounds of the kind which release diffusible dyes without receiving any electron (that is, without being reduced) or after receiving at least one electron (that is, after being reduced) during the photographic processing under an alkaline condition. Specific examples of the compounds of the abovedescribed kind are described in published unexamined Japanese Patent Applications Nos. 111628/74, 63618/76, 4819/77, 69033/78, 110827/78, 110828/78 and 130927/79.

Specific examples of yellow dye image-providing compounds which can be used in the present invention include those described in published examined Japanese Patent Application No. 2618/74; U.S. Pat. No. 3,309,199; published examined Japanese Patent Application No. 12140/82; published unexamined Japanese Patent Applications Nos. 114930/76, 111344/79, 16130/81 and 71072/81: published unexamined Japanese Patent application No. 79031/79: published unexamined Japanese Patent Applications Nos. 64036/78 and 23527/79: U.S. Pat. Nos. 4,148,641 and 4,148,643; and *Research Disclosure*, 17630 (1978) and 16475 (1977).

Specific examples of magenta dye image-providing compounds which can be used in the present invention include those described in U.S. Pat. No. 3,453,107; published examined Japanese Patent Application No. 43950/71 and published unexamined Japanese Patent Application No. 106727/77: U.S. Pat. Nos. 3,932,380; 3,931,144 and 3,932,308; and published unexamined Japanese Patent Applications Nos. 115528/75, 106727/77, 23628/78, 65034/79, 36804/80, 16133/79, 4028/80, 73057/81, 71060/81 and 134/80: and published unexamined Japanese Patent Applications No. 35533/78 and U.S. Pat. Nos. 4,207,104 and 4,287,292.

Specific examples of cyan dye image-providing compounds which can be used in the present invention include those described in published examined Japanese Patent application No. 32130/73 and published unexamined Japanese Patent application No. 8827/77; published unexamined Japanese Patent Applications Nos. 126331/74, 109928/76, 99431/79, 149328/78, 8826/77, 47823/78, 143323/78, 99431/79 and 71061/81; published unexamined Japanese Patent Applications Nos. 64035/78 and 121125/79; U.S. Pat. Nos. 4,142,891; 4,195,994; 4,147,544 and 4,148,642; and European Pat. Nos. 53,037 and 53,040; and *Research Disclosure*, 17630 (1978), 16475 (1975) and 16475 (1977).

The compounds of the present invention can also be employed in color photography conforming to the silver dye bleach process as described in T. H. James (editor), *The Theory of the Photographic Process*, 4th ed., chaper 12, pages 363–366 (Title: *Principles and Chemistry of Color Photography IV, Silver Dye Bleach Process*), Macmillan, New York (1977).

Moreover, the compounds of the present invention can be employed in black and white photosensitive materials. Suitable examples of such materials include Medical X-ray films for direct photographing, black and white films for general photographing, lithographic films, scanner films and so on.

Silver halide photographic materials to which the present invention can be applied do not have any particular restrictions as to, e.g., the process of making their silver halide emulsions, halogen constituents, the crystal habit of their silver halide grains, the grain size of their silver halides, and the kind of their constituents such as a chemical sensitizer, an antifoggant, a stabilizer, a surface active agent, a gelatin hardener, a hydrophilic colloidal binder, a matting agent, dyes, sensitizing dyes, a discoloration inhibitor, a color-mixing inhibitor, a polymer latex, a brightening agent, an antistatic agent, etc. For details of the above-described items, *Research Disclosure*, vol. 176, pp. 22–31 (December 1978) can be, for example, referred to.

Further, no particular restrictions are put on the way to expose and the way to develop the silver halide photographic materials of the present invention. Methods and processing solutions as described in, for example, *Research Disclosure*, supra, pp. 28–30 can be applied to the photographic materials of the present invention. The photographic processing may be either the photographic processing for forming a silver image (black and white photographic processing) or that for forming dye image (color photographic processing), if desired. A processing temperature is preferably selected from the range of 18° C. to 50° C. Of course, temperatures lower than 18° C. or those higher than 50° C. may be employed.

Developing solutions to be employed for black and white photographic processing can contain known developing agents. Suitable examples of known developing agents include dihydroxybenzenes (e.g., hydroquinones), 3-pyrazolidones (e.g., 1-phenyl-3-pyrazolidone), aminophenols (e.g., N-methyl-p-aminophenol) and so on. These developing agents may be employed independently or in a combination of two or more thereof. In addition to such a developing agent, a developing solution may generally contain known preservative, alkali agent, pH buffer and antifoggant and optinally, a dissolution aid, a color toning agent, a development accelerator, a surface active agent, a defoaming agent, a water softener, a hardener, a viscosity providing agent and so on.

To the photographic emulsion of the present invention, a so-called "lithographic type" of development processing can be applied. "Lithographic type" of development processing signifies the processing in which in order to effect the photographic reproduction of line images or the photographic reproduction of halftone images by means of dots, dihydroxybenzenes are generally used as a developing agent and the development step is made to proceed infectiously under the condition that the concentration of sulfite ion is maintained at a low concentration (the details of which are described in L. F. A. Mason, *Photographic Processing Chemistry*, pp. 163-165, Focal Press, London (1966)).

To the case of forming dye images, conventional methods can be applied. For instance, a nega-posi process (as described in *Journal of the Society of Molten Picture and Television Engineers*, vol. 61, pp. 667-701 (1953)); a color reversal process which comprises forming negative silver image by development with a developing solution containing a black and white developing agent, subjecting the silver image to uniform exposure at least once or to another proper fogging treatment and subsequently, carrying out color development to produce positive dye image; a silver dye bleach process which comprises exposing dye-containing photographic emulsions to light, developing the emulsions to produce silver images, and bleaching the dyes using the silver images as a bleaching catalyst; and so on can be employed.

A color developing solution is, in general, an alkaline aqueous solution containing a color developing agent. Suitable examples of color developing agents which can be used include known primary aromatic amine developers, such as phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfoamidoethylaniline, 4-amino-3-methyl-N-ethyl-N-$\beta$-methoxyethylaniline, etc.).

In addition to the above-described compounds, those described in L. F. A. Mason, *Photographic Processing Chemistry*, pp. 226-229, Focal Press, London (1966), U.S. Pat. Nos. 2,193,015 and 2,592,364, and published unexamined Japanese Patent Application No. 64933/73 can be also used as a color developing agent.

After the color development processing, photographic emulsion layers are generally subjected to a bleach processing. The bleach processing may be carried out simultaneously with a fixation processing, or separately therefrom. Suitable examples of a bleaching agent include compounds of polyvalent metals such as Fe(III), Co(IV), Cr(VI), Cu(II) and so on; peroxy acids; quinones; nitroso compounds; and so on.

Now, the present invention will be illustrated in more detail by reference to the following examples.

EXAMPLE 1

In order to evaluate the effectiveness of the antifoggant precursors of the present invention, samples A to I were prepared as follows: One of the antifoggant precursors of the present invention or one of antifoggants corresponding thereto, respectively (for comparison), which are set forth in Table 1, was dissolved in tricresyl phosphate together with the coupler (Cp-1), emulsified and added to the silver halide emulsion. The resulting emulsion was coated on a cellulose triacetate support where a subbing layer was provided. The coverage of each constituent was expressed in terms of $g/m^2$ or $mol/m^2$ and designated in parentheses.

(1) Emulsion Layer
  Negative type silver iodobromide emulsion having a grain size of 1.4$\mu$ (silver: $1.6 \times 10^{-2}$ mol/m$^2$)
  Magenta Coupler Cp-1 ($1.33 \times 10^{-3}$ mol/m$^2$)
  Antifoggant or antifoggant precursor of the present invention (one which set forth in Table 1)
  Gelatin (2.50 g/m$^2$)
(2) Protective Layer
  Gelatin (1.30 g/m$^2$)
  Sodium 2,4-dichloro-6-hydroxy-s-triazine (0.50 g/m$^2$)

These films were allowed to stand for 14 hours under the conditions of 40° C. and relative humidity of 70%. Thereafter, they were subjected to imagewise exposure for sensitometry and then, to a color development processing.

| Steps for Color Development | Time | Temperature |
| --- | --- | --- |
| 1. Color development | 3'15" | 38° C. |
| 2. Bleaching | 6'30" | " |
| 3. Washing | 2' | " |
| 4. Fixation | 4' | " |
| 5. Washing | 4' | " |
| 6. Stabilization | 1' | " |

Compositions of processing solutions employed in the above-described steps are described below.

| Color Developing Solution: | |
| --- | --- |
| Water | 800 ml |
| 4-(N—ethyl-n-hydroxyethyl)amino-2-methyl-aniline sulfate | 5 g |
| Sodium Sulfate | 5 g |
| Hydroxylamine Sulfate | 2 g |
| Potassium Carbonate | 30 g |
| Potassium Hydrogencarbonate | 1.2 g |
| Potassium Bromide | 1.2 g |
| Sodium Chloride | 0.2 g |
| Trisodium Nitrilotriacetate | 1.2 g |
| Water to make | 1 liter |
| | (pH = 10.1) |
| Bleaching Solution: | |
| Water | 800 ml |
| Ammonium Ethylenediaminetetraacetonato-ferrate (III) | 100 g |
| Disodium Ethylenediaminetetraacetate | 10 g |
| Potassium Bromide | 150 g |
| Acetic Acid | 10 g |
| Water to make | 1 liter |
| | (pH = 6.0) |
| Fixing Solution: | |
| Water | 800 ml |
| Ammonium Thiosulfate | 150 g |
| Sodium Sulfite | 10 g |
| Sodium Hydrogensulfite | 2.5 g |

-continued

| | |
|---|---|
| Water to make | 1 liter (pH = 6.0) |
| Stabilizing Solution: | |
| Water | 800 ml |
| Formaline (37%) | 5 ml |
| Driwell (trade name of a surfactant manufactured by Fuji Photo Film Co., Ltd.) | 3 ml |
| Water to make | 1 liter |

Photographic properties obtained are shown in Table 1.

TABLE 1

| Sample | Antifoggant Precursor of This Invention or Antifoggant | Amount Added (mol/m$^2$) | Fog | Gamma | Relative Sensitivity | Maximum Coloration Density |
|---|---|---|---|---|---|---|
| A | not added | — | 0.13 | 0.82 | 100 | 1.60 |
| B | Compound (1) | $2.2 \times 10^{-6}$ | 0.07 | 0.71 | 92 | 1.48 |
| C | Compound (5) | $2.2 \times 10^{-6}$ | 0.07 | 0.80 | 95 | 1.52 |
| D | Compound (6) | $4.4 \times 10^{-6}$ | 0.08 | 0.79 | 98 | 1.56 |
| E | Compound (14) | $2.2 \times 10^{-5}$ | 0.11 | 0.82 | 102 | 1.60 |
| F | Compound (16) | $2.2 \times 10^{-5}$ | 0.10 | 0.80 | 100 | 1.57 |
| G* | Compound (A-1) | $2.2 \times 10^{-6}$ | 0.05 | 0.40 | 25 | 0.93 |
| H* | Compound (A-2) | $4.4 \times 10^{-6}$ | 0.03 | 0.51 | 34 | 1.08 |
| I* | Compound (A-3) | $2.2 \times 10^{-5}$ | 0.08 | 0.64 | 50 | 1.35 |

*Examples for comparison.

As can be seen clearly from the results shown in Table 1, the samples B to F which contained the antifoggant precursors according to the present invention were able to depress the generation of fog while scarcely lowering sensitivity, gradation and coloration density.

The antifoggants (A-1) to (A-3) employed for comparison, and the coupler (Cp-1) incorporated in the above-described samples are illustrated below.

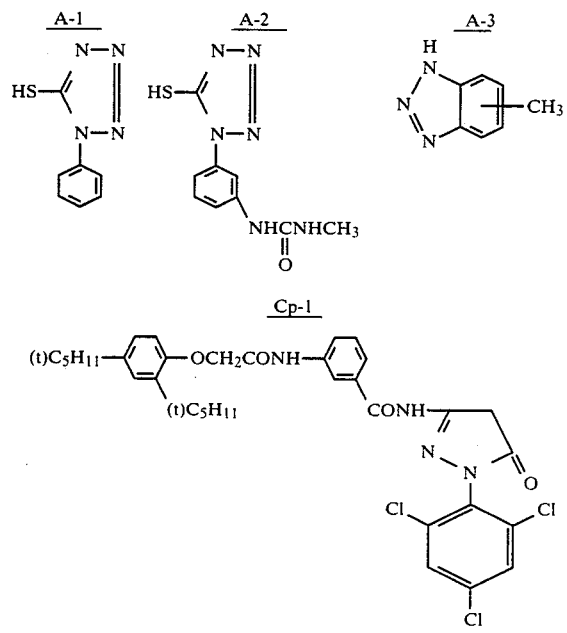

EXAMPLE 2

On a transparent polyethylene terephthalate film support, were coated layers (1) to (3) described below in this order to prepare a cover sheet.

(1) Layer containing 11 g/m$^2$ of acrylic acid-butylacrylate (80:20 by weight) copolymer and 0.22 g/m$^2$ of 1,4-bis(2,3-epoxypropoxy)-butane.

(2) Layer containing 4.3 g/m$^2$ of acetyl cellulose (which produced 36.6 g of acetic acid when hydrolyzed in an amount of 100 g), 0.23 g/m$^2$ of a ring cleavage product obtained by making methanol act upon styrene-maleic anhydride copolymer (copolymerization ratio; 60:40 by weight, molecular weight; about 50,000), and a compound set forth in Table 2 in a coverage of 65 meq./m$^2$ based on the development restrainer.

(3) Layer having a thickness of 2μ which was formed by coating a latex mixture prepared by mixing a latex of styrene-n-butylacrylate-acrylic acid-N-methylolacrylamide (49.7:42.3:3:5) by mole) copolymer with a latex of methylmethacrylateacrylic acid-N-methylolacrylamide (93:4:3 by weight) copolymer in a ratio of 6 (the former) to 4 (the latter) based on the amount of solid.

On a transparent polyethylene terephthalate film support, were coated layers described below in this order to prepare a light-sensitive sheet.

(1) Mordanting layer containing 3.0 g/m$^2$ of gelatin, and 3.0 g/m$^2$ of a mordant of the copolymer latex illustrated below.

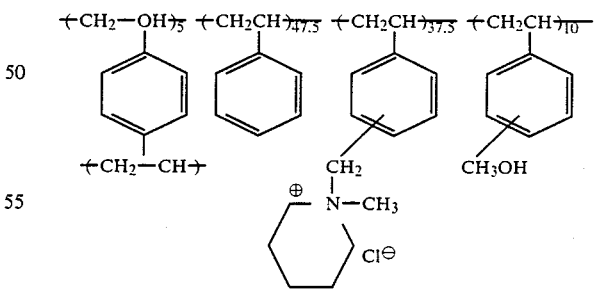

(2) White reflecting layer containing 18 g/m$^2$ of titanium dioxide and 2.0 g/m$^2$ of gelatin.

(3) Light intercepting layer containing 2.0 g/m$^2$ of carbon black and 1.0 g/m$^2$ of gelatin.

(4) Layer containing 0.44 g/m$^2$ of a cyan dye releasing redox compound of the structural formula shown below, 0.09 g/m$^2$ of tricyclohexyl phosphate, 0.008 g/m$^2$ of 2,5-di-t-pentadecylhydroquinone, and 0.8 g/m$^2$ of gelatin.

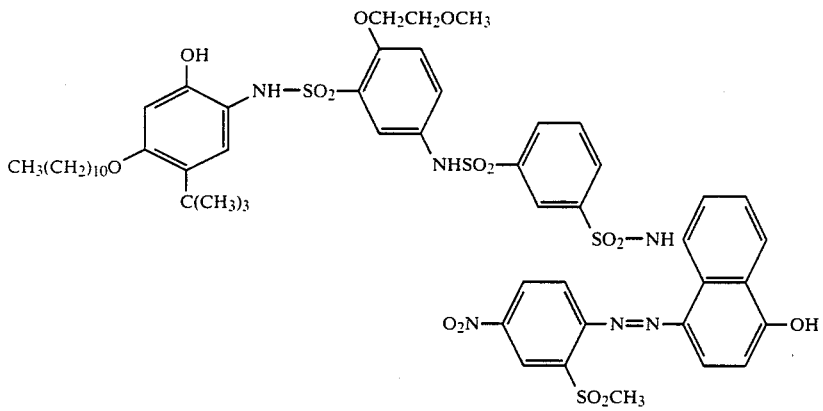

(5) Red-sensitive emulsion layer containing a red-sensitive internal latent image type direct positive silver bromide emulsion (containing 1.03 g/m² of silver), 1.2 g/m² of gelatin, 0.04 mg/m² of a neucleating agent of the structural formula shown below, and 0.13 g/m² of 2-sulfo-5-n-pentadecylhydroquinone sodium salt.

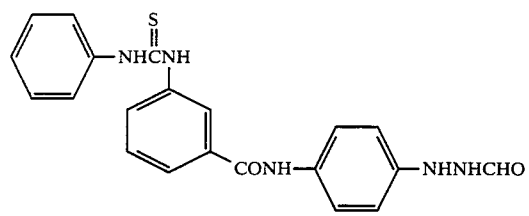

(6) Layer containing 0.43 g/m² of 2,5-di-t-pentadecylhydroquinone, 0.1 g/m² of trihexyl phosphate, and 0.4 g/m² of gelatin.

(7) Layer containing 0.21 g/m² of a magenta dye releasing redox compound of the structural formula I shown below, 0.11 g/m² of another magenta dye releasing redox compound of the structural formula II shown below, 0.08 g/m² of tricyclohexyl phosphate, 0.009 g/m² of 2,5-di-t-pentadecylhydroquinone, and 0.9 g/m² of gelatin.

silver bromide emulsion (containing 0.82 g/m² of silver, 0.97 mg/m² of Dye-A illustrated below, and 1.29 mg/m² of Dye-B illustrated below), 0.9 g/m² of gelatin, 0.03 mg/m² of the same nucleating agent as incorporated in the layer (5), and 0.08 g/m² of 2-sulfo-5-n-pentadecylhydroquinone sodium salt.

Dye-A

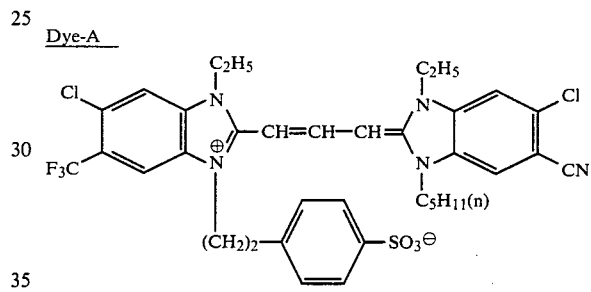

Dye-B

Formula I

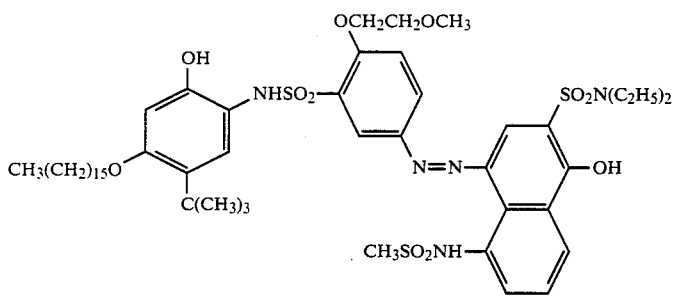

Formula II

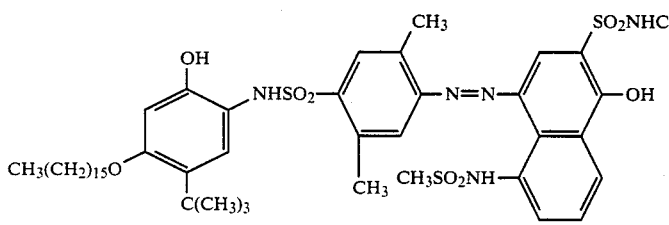

(8) Green-sensitive emulsion layer containing a green-sensitive internal latent image-type direct positive

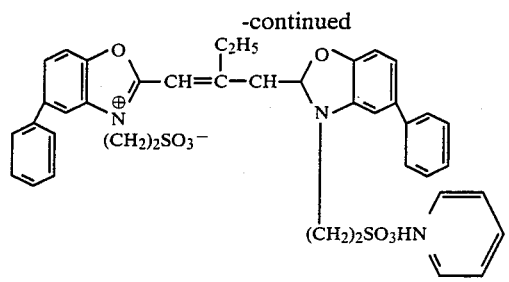

(9) The same layer as the layer (6).

(10) Layer containing 0.53 g/m² of an yellow dye releasing redox compound of the structural formula shown below, 0.13 g/m² of tricyclohexyl phosphate, 0.014 g/m² of 2,5-di-t-pentadecylhydroquinone, and 0.7 g/m² of gelatin.

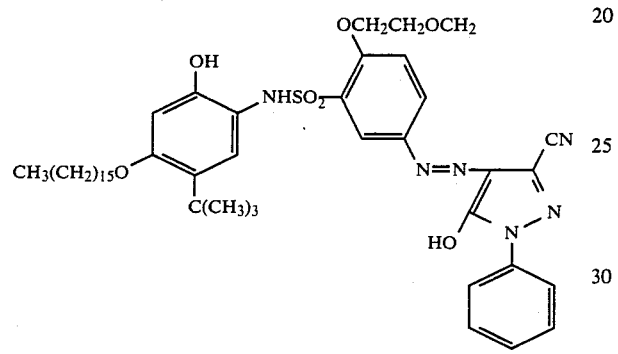

(11) Blue-sensitive emulsion layer containing a blue-sensitive internal latent image type direct positive silver bromide emulsion (containing 1.09 g/m² of silver), 1.1 g/m² of gelatin, 0.04 mg/m² of the same neucleating agent as incorporated in the layer (5), and 0.07 g/m² of 2-sulfo-5-n-pentadecylhydroquinone sodium salt.

(12) Layer containing 1.0 g/m² of gelatin.

The light-sensitive sheet was exposed to light through a color test chart and thereon, the cover sheet was superposed. Then, the processing solution described below was spread in 85μ thickness between the two sheets (with the aid of pressure-applying rollers). The spread was carried out at a temperature of 35° C.

Results of examination in the maximum density and minimum density are shown in Table 2. As can be seen from Table 2, the compounds of the present invention enabled an increase in maximum density and the control of minimum density to a low level.

On the other hand, the unblocked 1-phenyl-5-mercaptotetrazole which was employed for comparison was found to suffer from the defect that it caused a marked decrease in maximum density.

| Processing Solution: | |
|---|---|
| 1-p-Tolyl-4-hydroxymethyl-4-methyl-3-pyrazolidone | 6.9 g |
| Methylhydroquinone | 0.3 g |
| 5-Methylbenzotriazole | 3.5 g |
| Sodium Sulfite (Anhydrous) | 0.2 g |
| Sodium Salt of Carboxymethyl Cellulose | 58 g |
| Potassium Hydroxide (28% Aqueous Solution) | 200 cc |
| Benzyl Alcohol | 1.5 cc |
| Carbon Black | 150 g |
| Water | 685 cc |

TABLE 2

| Cover Sheet No. | Compound Added | Maximum Density | | | Minimum Density | | |
|---|---|---|---|---|---|---|---|
| | | B | G | R | B | G | R |
| 1 | (Blank) | 1.60 | 1.78 | 1.88 | 0.28 | 0.30 | 0.45 |
| 2 | Compound (9) | 1.78 | 1.96 | 1.96 | 0.26 | 0.27 | 0.40 |
| 3 | Compound (2) | 1.78 | 1.97 | 1.97 | 0.26 | 0.27 | 0.39 |
| 4 | 1-Phenyl-5-mercaptotetrazole | 1.21 | 1.57 | 1.85 | 0.24 | 0.25 | 0.38 |

B: Blue
G: Green
R: Red

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material which comprises a light-sensitive silver halide emulsion layer having associated therewith a blocked photographic agent, said blocked photographic agent being represented by the following general formula (I):

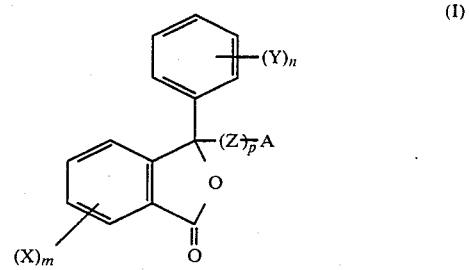

wherein A represents a photographic agent moiety which is attached to a blocking moiety through a hetero atom; Z represents a divalent linkage group; p represents 0 or 1; X and Y each represents a halogen atom, an alkyl group, an alkenyl group, an aryl group, an alkoxy group, an aryloxy group, an acyloxy group, a carboxylic acid ester group, an amino group, a carbonamido group, a sulfonamido group, an ureido group, an aminosulfonamido group, a carbamate group, a carboxy group, an alkoxycarbonyl group, an aryloxycarbonyl, a carbamoyl group, an acyl group, a sulfo group, an alkylsulfonyl group, an arylsulfonyl group, a sulfamoyl group, a cyano group or a nitro group, and they may be the same as or different from each other; m represents an integer of 0 to 4; and n represents an integer of 0 to 5.

2. A silver halide photographic light sensitive material as claimed in claim 1, wherein said photographic agent is selected from the group consisting of an antifoggant, a development restrainer, a developing agent, an auxiliary developer, a fogging agent, a silver halide solvent, a bleach accelerating agent and a dye.

3. A silver halide photographic light-sensitive material as claimed in claim 1, wherein said photographic agent is selected from the group consisting of mercaptotetrazoles, mercaptotriazoles, mercatopyrimidines, mercaptobenzimidazoles, mercaptothiadiazoles, benzotriazoles and indazoles.

4. A silver halide photographic light-sensitive material as claimed in claim 1, wherein said photographic agent is selected from the group consisting of p- phenylenediamines, hydroquinones, p-aminophenols and pyrazolidones.

5. A silver halide photographic light-sensitive material as claimed in claim 1, wherein said photographic agent is selected from a group consisting of hydrazines and hydrazides.

6. A silver halide photographic light-sensitive material as claimed in claim 1, wherein said photographic agent is an agent selected from the group consisting azo dyes and azomethine dyes.

7. A silver halide photographic light-sensitive material as claimed in claim 1, wherein p of said blocked photographic agent represented by the general formula (I) is 0.

8. A silver halide photographic light-sensitive material as claimed in claim 1, wherein A of said blocked photographic agent represented by the general formula (I) is a phenyltetrazolylthio group.

9. A silver halide photographic light-sensitive material as claimed in claim 1, wherein said material is a diffusion transfer silver halide photographic light-sensitive material comprising (1) a light-sensitive element comprising a support having thereon said light-sensitive silver halide emulsion layer having associated therewith a dye image-providing material, and (2) an image receiving element wherein a diffusible dye produced in an imagewise manner from said dye image-providing material is fixed to form an image.

10. A silver halide photographic light-sensitive material as claimed in claim 9, which has at least one hydrophilic colloidal layer other than said silver halide emulsion layer.

11. A silver halide photographic light-sensitive material as claimed in claim 9, which contains an alkaline processing composition with which the light-sensitive silver halide emulsion which is imagewise exposed is developable.

12. A silver halide photographic light-sensitive material as claimed in claim 11, which further has a neutralizing function for neutralizing said alkaline processing composition.

13. A silver halide photographic light-sensitive material as claimed in claim 1, wherein said material is a color diffusion transfer silver halide photographic light-sensitive material comprising (1) a light-sensitive sheet comprising a transparent support having thereon (i) an image receiving element which enables fixation of diffusible dyes to form an image, (ii) a light-reflecting white layer, (iii) a light intercepting layer, and (iv) at least one silver halide emulsion layer having associated therewith a dye image-providing material, (2) an alkaline processing composition which enables the development of said light-sensitive element after imagewise exposure, and (3) a cover sheet comprising a support having thereon a layer having a neutralizing function for neutralizing said alkaline processing composition.

14. A silver halide photographic light-sensitive material as claimed in claim 13, wherein said cover sheet contains the blocked photographic agent represented by the general formula (I).

15. A silver halide photographic light-sensitive material as claimed in claim 1, wherein said silver halide emulsion is an internal latent image type direct positive emulsion.

16. A silver halide photographic light-sensitive material as claimed in claim 1, wherein said dye image-providing material is a DRR compound and that, the silver halide emulsion to be associated with said dye image-providing material is an internal latent image type direct positive emulsion.

17. A silver halide photographic light sensitive material as claimed in claim 1, wherein said blocked photographic agent is an antifoggant and the blocked photographic agent is contained in the photographic material in an amount of $10^{-8}$ to $10^{-1}$ mole per mole of silver in the silver halide emulsion.

18. A silver halide photographic light sensitive material as claimed in claim 1, wherein said blocked photographic agent is a development restrainer and the blocked photographic agent is contained in the photographic material in an amount of $10^{-8}$ to $10^{-1}$ mole per mole of silver in the silver halide emulsion.

19. A silver halide photographic light sensitive material as claimed in claim 1, wherein said blocked photographic agent is a developing agent and the blocked photographic agent is contained in the photographic material in an amount of $10^{-2}$ to 10 mole per mole of silver in the silver halide emulsion.

20. A silver halide photographic light sensitive material as claimed in claim 1, wherein said blocked photographic agent is an auxiliary developer of a pyrazolidone type and the blocked photographic agent is contained in the photographic material in an amount of $10^{-4}$ to 10 mole per mole of silver in the silver halide emulsion.

21. A silver halide photographic light sensitive material as claimed in claim 1, wherein said blocked photographic agent is a fogging agent and the blocked photographic agent is contained in the photographic material in an amount of $10^{-2}$ to $10^{-6}$ mole per mole of silver in the silver halide emulsion.

22. A silver halide photographic light sensitive material as claimed in claim 1, wherein said blocked photographic agent is a silver halide solvent and the blocked photographic agent is contained in the photographic material in an amount of $10^{-3}$ to 10 mole per mole of silver in the silver halide emulsion.

23. A silver halide photographic light sensitive material as claimed in claim 1, wherein said blocked photographic agent is a bleach accelerating agent and the blocked photographic agent is contained in the photographic material in an amount of $10^{-5}$ to $10^{-1}$ mole per mole of silver in the silver halide emulsion.

24. A silver halide photographic light sensitive material as claimed in claim 1, wherein said blocked photographic agent is a dye and the blocked photographic agent is contained in an amount of $10^{-3}$ to 1 mole per mole of silver in the silver halide emulsion.

25. A silver halide photographic light sensitive material as claimed in claim 1, wherein said blocked photographic agent is a cooling material for color diffusion transfer photography and the blocked photographic agent is contained in an amount of $10^{-3}$ to 1 mole per mole of silver in the silver halide emulsion.

* * * * *